United States Patent [19]

Terranova et al.

[11] Patent Number: 5,704,948
[45] Date of Patent: Jan. 6, 1998

[54] COMPOSITIONS FOR DYEING KERATINOUS FIBERS AND KERATINOUS FIBER DYEING PROCESSES WITH DERIVATIVES OF 4-HYDROXYINDOLE AND OXIDATION BASES

[75] Inventors: Eric Terranova, Asnieres; Aziz Fadli, Le Blanc Mesnil; Alain Lagrange, Coupvray, all of France

[73] Assignee: L'Oreal, Paris, France

[21] Appl. No.: 678,981

[22] Filed: Jul. 12, 1996

[30] Foreign Application Priority Data

Jul. 13, 1995 [FR] France ................... 95-08566

[51] Int. Cl.$^6$ ................................................ A61K 7/13
[52] U.S. Cl. ................... 8/409; 8/407; 8/408; 8/423
[58] Field of Search .................... 8/408, 409, 423, 8/407

[56] References Cited

U.S. PATENT DOCUMENTS 3,503,990  3/1970  Schoen et al. ................ 260/326.12
4,932,977  6/1990  Schultz ................................. 8/423
5,609,649  3/1997  Junino et al. ........................ 8/409

FOREIGN PATENT DOCUMENTS

A-428441  5/1991  European Pat. Off. .
3031709   4/1982  Germany .
WO-A-
9217157  10/1992  WIPO .

OTHER PUBLICATIONS

English language Derwent Abstract of EP-A-428441, May/1991.
English language Derwent Abstract of WO-A-9217157, Oct./1992.

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A composition for the oxidation dyeing of keratinous fibers containing at least one coupler selected from N-substituted 4-hydroxyindole compounds and acid addition salt thereofs and at least one oxidation base, N-substituted 4-hydroxyindole compounds, a process for synthesizing these substituted compounds, their use as couplers for the oxidation dyeing of keratinous fibers in combination with at least one oxidation base, as well as dyeing processes employing them.

21 Claims, No Drawings

COMPOSITIONS FOR DYEING KERATINOUS FIBERS AND KERATINOUS FIBER DYEING PROCESSES WITH DERIVATIVES OF 4-HYDROXYINDOLE AND OXIDATION BASES

The present invention is directed to a composition for the oxidation dyeing of keratinous fibers, and in particular human keratinous fibers such as hair, comprising, at least one coupler selected from N-substituted compounds of 4-hydroxyindole and acid addition salts of these 4-hydroxyindoles, and at least one oxidation base.

It is known to dye keratinous fibers, and in particular, human hair, with dyeing compositions containing oxidation dye precursors, especially ortho- or para-phenylenediamines, ortho- or para-aminophenols, and heterocyclic compounds, which are generally referred to as oxidation bases. Oxidation dye precursors, or oxidation bases, are colorless or faintly colored compounds which, when combined with oxidizing products, can give rise, by an oxidative condensation process, to colored and coloring compounds.

It is also known that the shades obtained with these oxidation bases can be varied by combining them with dyeing couplers or modifiers; the modifiers being chosen, in particular, from aromatic meta-diamines, meta-aminophenols, meta-diphenols and some heterocyclic compounds such as indole compounds.

The variety of molecules employed as oxidation bases and as couplers enables a rich palette of colors to be obtained.

The so-called "permanent" dyeing obtained by means of these oxidation needs, moreover, to satisfy a number of requirements. These oxidation dyes must have no drawback from a toxicological standpoint, and must enable shades to be obtained of a desired intensity and need to display good staying power when exposed to external agents, such as light, inclement weather, washing, permanent-waving, perspiration, and friction.

The dyes must also enable white hair to be covered, and lastly, must be the least selective possible, that is to say, must allow only the smallest possible deviations of coloration to be obtained over the entire length of the same keratinous fiber, which may, in effect, be differently sensitized, i.e. damaged, between its end and its root.

There have been proposed, in particular in European Patent Application No. EP-A-428 441, compositions for the oxidation dyeing of keratinous fibers containing:, as couplers, at least one 4-hydroxyindole derivative which can be N-substituted with a $C_1$–$C_4$ alkyl radical. Such compositions make it possible to obtain varied ranges of shades but they are not, however, entirely satisfactory, especially from the point of view of the staying power of the colorations obtained with respect to various external agents to which the hair may be subjected, in particular, light.

The Inventors have discovered that it is possible to obtain new powerful dyes, which show little selectivity and are particularly resistant, and are capable of creating intense colorations in varied shades, by using specific 4-hydroxyindole derivatives, in particular, N-substituted derivatives. These compounds can furthermore be easily synthesized. This discovery underlies the present invention.

A subject of the invention is a thus composition for dyeing keratinous fibers, and in particular human keratinous fibers such as hair, which comprises, in a medium suitable for dyeing:

at least one N-substituted derivative of 4-hydroxyindole or an acid addition salt thereof of formula (I), as a coupler:

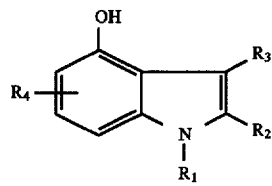

in which:

$R_1$ represents a $C_1$–$C_4$ monohydroxyalkyl radical; a $C_2$–$C_4$ polyhydroxyalkyl radical; a $C_1$–$C_4$ alkoxy($C_1$–$C_4$)-alkyl radical; a $C_1$–$C_4$ hydroxyalkoxy($C_1$–$C_4$)alkyl radical; a $C_1$–$C_4$ aminoalkyl radical; a $C_1$–$C_4$ aminoalkyl radical whose amine is mono- or disubstituted with a $C_1$–$C_4$ alkyl group, with an acetyl group, with a $C_1$–$C_4$ monohydroxyalkyl group or with a $C_2$–$C_4$ polyhydroxyalkyl group; a $C_1$–$C_4$ alkyl($C_1$–$C_4$)thioalkyl radical; a $C_1$–$C_4$ monohydroxyalkyl($C_1$–$C_4$)thioalkyl radical; a $C_2$–$C_4$ polyhydroxyalkyl($C_1$–$C_4$)thioalkyl radical; a $C_1$–$C_4$ carboxyalkyl radical; a $C_1$–$C_4$ alkoxy($C_1$–$C_4$)-carbonylalkyl radical; a $C_1$–$C_4$ acetylaminoalkyl radical; a $C_1$–$C_4$ cyanoalkyl radical; a $C_1$–$C_4$ trifluoroalkyl radical; a $C_1$–$C_4$ haloalkyl radical; a $C_1$–$C_4$ phosphoalkyl radical; or a $C_1$–$C_4$ sulphoalkyl radical;

$R_2$ and $R_3$, which are identical or different, represent a hydrogen or halogen atom; or a $C_1$–$C_4$ alkyl, a carboxyl, a $C_1$–$C_4$ alkoxycarbonyl or a formyl radical;

$R_4$ represents a hydrogen or halogen atom; a $C_1$–$C_4$ alkyl radical; a $C_1$–$C_4$ alkoxy radical; an acetylamino radical; a $C_1$–$C_5$ monohydroxyalkyl radical; a $C_2$–$C_4$ polyhydroxyalkyl radical; a $C_1$–$C_4$ alkoxy($C_1$–$C_4$)alkyl radical; a thiophene radical; a furan radical; a phenyl radical; a $C_7$–$C_{10}$ aralkyl radical; a phenyl or $C_7$–$C_{10}$ aralkyl radical which is substituted with a halogen atom, a $C_1$–$C_4$ alkyl radical, a trifluoromethyl radical, a $C_1$–$C_4$ alkoxy radical, an amino radical or an amino radical mono- or disubstituted with a $C_1$–$C_4$ alkyl radical; a $C_1$–$C_4$ alkyl($C_1$–$C_4$)aminoalkyl radical; or a $C_1$–$C_4$ dialkyl($C_1$–$C_4$)aminoalkyl radical; and at least one oxidation base.

In the above formula (I), the alkyl and alkoxy groups may be linear or branched and the halogen atoms may be selected from chlorine, bromine, iodine and fluorine.

The couplers of formula (I) in accordance with the invention differ from the known products of the above-mentioned European Patent No. EP-A-428 441, in the nature of the $R_1$ substituent in the 1-N position.

The colorations obtained with the dyeing composition according to the invention are varied and are of powerful shades displaying little selectivity and having excellent resistance properties, both with respect to environmental agents such as light and inclement weather, and with respect to perspiration and different treatments which hair may undergo, such as shampooing and permanent reshaping. These properties are particularly remarkable with respect to light.

Among the N-substituted derivatives of 4-hydroxyindole of formula (I), which can be used as couplers in the compositions according to the invention, there may preferably be mentioned:

4-hydroxy-1-N-(β-hydroxyethyl)indole,
4-hydroxy-1-N-(β-hydroxypropyl)indole,
1-N-(β,γ-dihydroxypropyl)-4-hydroxyindole,
4-hydroxy-1-N-(β-hydroxyethyl)-5-methylindole,
4-hydroxy-1-N-(β-hydroxypropyl)-5-methylindole,
1-N-(β,γ-dihydroxypropyl)-4-hydroxy-5-methylindole,
4-hydroxy-1-N-(β-hydroxyethyl)-6-methylindole, 4-hydroxy-1-N-(β-hydroxypropyl)-6-methylindole,
1-N-(β,γ-dihydroxypropyl)-4-hydroxy-6-methylindole,
5-benzyl-4-hydroxy-1-N-(β-hydroxyethyl)indole,
5-benzyl-4-hydroxy-1-N-(β-hydroxypropyl)indole,
5-benzyl-1-N-(β,γ-dihydroxypropyl)-4-hydroxyindole,
4-hydroxy-1-N-(β-hydroxyethyl)-5-β-hydroxyethylindole,
4-hydroxy-5-β-hydroxyethyl-1-N-(β-hydroxypropyl)indole,
1-N-(β,γ-dihydroxypropyl)-4-hydroxy-5-γ-hydroxyethylindole,
4-hydroxy-1-N-(β-hydroxyethyl)-5-β,γ-dihydroxypropylindole,
4-hydroxy-1-N-(β-hydroxypropyl)-5-β,γ-dihydroxypropylindole,
1-N-(β,γ-dihydroxypropyl)-4-hydroxy-5-β,γ-dihydroxypropylindole,
1-N-(γ-dimethylaminopropyl)-4-hydroxyindole,
1-N-ethylaminoethyl-4-hydroxyindole,
and the acid addition salts of these compounds.

Among these N-substituted derivatives of 4-hydroxyindole, those which are more preferred include:
4-hydroxy-1-N-(β-hydroxyethyl)indole,
4-hydroxy-1-N-(β-hydroxypropyl)indole,
1-N-(β,γ-dihydroxypropyl)-4-hydroxyindole,
4-hydroxy-1-N-(β-hydroxyethyl)-5-methylindole,
1-N-(γ-dimethylaminopropyl)-4-hydroxyindole,
and the acid addition salts of these compounds.

The acid addition salts of the compounds of formula (I) which can be used as couplers in the dyeing compositions according to the invention are preferably chosen from hydrochlorides, hydrobromides, sulphates and tartrates.

The N-substituted derivative(s) of 4-hydroxyindole of formula (I) preferably represent approximately from 0.0005 to 12% by weight of the total weight of the dyeing composition, and still more preferably approximately from 0.005 to 6% by weight of this weight.

The nature of the oxidation base(s) which can be used in the dyeing composition according to the invention is not critical. This or these oxidation base(s) are preferably chosen from para-phenylenediamines, bis-phenylalkylenediamines, para-aminophenols, ortho-aminophenols, heterocyclic bases, and their acid addition salts.

Among the para-phenylenediamines which are preferably used as oxidation bases in the dyeing composition according to the invention, there may be mentioned the compounds of formula (II) and their acid addition salts:

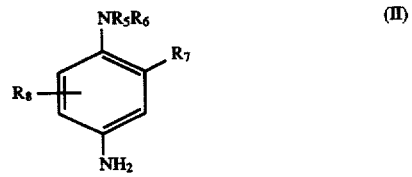

in which:

$R_5$ represents a hydrogen atom; or a $C_1$-$C_4$ alkyl, $C_1$-$C_4$ monohydroxyalkyl, $C_2$-$C_4$ polyhydroxyalkyl or alkoxy-($C_1$-$C_4$)alkyl($C_1$-$C_4$) radical;

$R_6$ represents a hydrogen atom; or a $C_1$-$C_4$ alkyl, $C_1$-$C_4$ monohydroxyalkyl or $C_2$-$C_4$ polyhydroxyalkyl radical;

$R_7$ represents a hydrogen atom; a halogen atom, and preferably a chlorine atom; a $C_1$-$C_4$ alkyl, a sulpho, a carboxyl, a $C_1$-$C_4$ monohydroxyalkyl or a $C_1$-$C_4$ hydroxyalkoxy radical;

$R_8$ represents a hydrogen atom or a $C_1$-$C_4$ alkyl radical.

In the above formula (II), when $R_7$ is other than a hydrogen atom, $R_5$ and $R_6$ preferably represent a hydrogen atom and $R_7$ is preferably identical to $R_8$. When $R_7$ represents a halogen atom, $R_5$, $R_6$ and $R_8$ preferably represent a hydrogen atom.

Among the para-phenylenediamines of formula (II) above, there may be mentioned more particularly para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 4-amino-1-(β-methoxyethyl)aminobenzene, 2-chloro-para-phenylenediamine, and their acid addition salts.

Among the bis-phenylalkylenediamines which are preferably used as oxidation bases in the dyeing composition according to the invention, there may be mentioned the compounds of formula (III) and their acid addition salts:

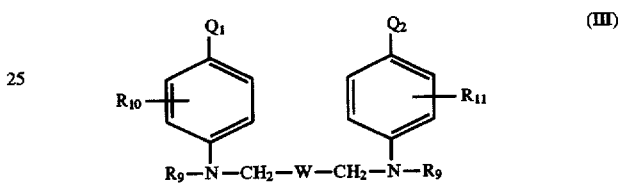

in which:

$Q_1$ and $Q_2$, which are identical or different, represent a hydroxyl radical or an $NHR_{12}$ radical in which $R_{12}$ represents a hydrogen atom or a $C_1$-$C_4$ alkyl radical; $R_9$ represents a hydrogen atom, a $C_1$-$C_4$ alkyl radical, a $C_1$-$C_4$ monohydroxyalkyl radical, a $C_2$-$C_4$ polyhydroxyalkyl or a $C_1$-$C_4$ aminoalkyl radical whose amino residue may be substituted;

$R_{10}$ and $R_{11}$, which are identical or different, represent a hydrogen, a halogen atom, or a $C_1$-$C_4$ alkyl radical;

W represents a radical selected from the group:

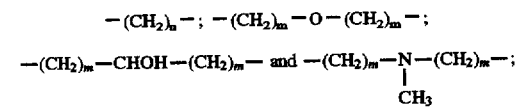

in which n is an integer ranging from 0 to 8 inclusive, and m is an integer ranging from 0 to 4 inclusive.

Among the bis-phenylalkylenediamines of formula (III) above, there may be mentioned more particularly N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-ethylaminophenyl)tetramethylenediamine, N,N'-bis(ethyl)-N,N'-bis(4'-amino-3'-methylphenyl)ethylenediamine, and their acid addition salts.

Among these bis-phenylalkylenediamines of formula (III), N,N'-bis(β-hydroxyethyl)-N,N'-bis(4'-aminophenyl)-1,3-diaminopropanol or one of its acid addition salts is particularly preferred.

Among the para-aminophenols which can be used as oxidation bases in the dyeing composition according to the invention, there may be mentioned the compounds of formula (IV) and their acid addition salts:

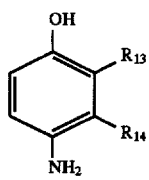

(IV)

in which:

$R_{13}$ represents a hydrogen atom; or a $C_1$–$C_4$ alkyl, $C_1$–$C_4$ monohydroxyalkyl, alkoxy($C_1$–$C_4$)alkyl($C_1$–$C_4$) or $C_1$–$C_4$ aminoalkyl radical; $R_{14}$ represents a hydrogen atom; a fluorine atom; or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or alkoxy($C_1$–$C_4$)alkyl($C_1$–$C_4$) radical; wherein at least one of the radicals $R_{13}$ or $R_{14}$ represents a hydrogen atom.

Among the para-aminophenols of formula (IV) above, there may be mentioned more particularly para-aminophenol, 4-amino-3-methylphenol, or 4-amino-3-fluorophenol, 4-amino-3-hydroxymethylphenol, 4-amino-2-methylphenol, 4-amino-2-hydroxymethyl-phenol, 4-amino-2-methoxymethylphenol, 4-amino-2-aminomethylphenol, 4-amino-2-(β-hydroxyethylaminomethyl)phenol, and their acid addition salts.

Among the ortho-aminophenols which are preferably used as oxidation bases in the dyeing composition according to the invention, there may be mentioned 2-aminophenol, 2-amino-1-hydroxy-5-methylbenzene, 2-amino-1-hydroxy-6-methylbenzene, 5-acetamido-2-aminophenol, and their acid addition salts.

Among the heterocyclic bases which are preferably used as oxidation bases in the dyeing composition according to the invention, there may be mentioned pyridine derivatives, pyrimidine derivatives, pyrazole derivatives, and their acid addition salts.

Among the pyridine derivatives, there may be mentioned more particularly, the compounds described for example in British Patent Nos. GB 1,026,978 and GB 1,153,196, the disclosures of which are incorporated herein by reference, such as 2,5-diaminopyridine, and their its addition salts.

Among the pyrimidine derivatives, there may be mentioned, more particularly, the compounds described for example in German Patent No. DE 2,359,399 or in Japanese Patent Nos. JP 88 169 571 and JP 91 333 495, the disclosures of which are incorporated herein by reference, such as 2,4,5,6-tetraaminopyrimidine, 4-hydroxy-2,5,6-triaminopyrimidine, and their acid addition salts.

Among the pyrazole derivatives, there may be mentioned, more particularly, the compounds described in German Patent Nos. DE 3,843,892 and DE 4,133,957 and International Patent Application Nos. WO 94/08969 and WO 94/08970, the disclosures of all of which are incorporated herein by reference, such as 4,5-diamino-1-methylpyrazole, 3,4-diaminopyrazole, and their acid addition salts.

According to the invention, the oxidation base(s) preferably represent approximately from 0.0005 to 12% by weight of the total weight of the dyeing composition, and still more preferably, approximately from 0.005 to 6% by weight of this weight.

The dyeing composition according to the invention may also contain one or more additional couplers that are different from the N-substituted derivatives of 4-hydroxyindole of formula (I) and/or one or more direct dyes so as to vary or enrich in glints the shades obtained with the oxidation bases.

The additional couplers which can be used in the composition according to the invention may be chosen from the couplers conventionally used in oxidation dyeing and among which there may be mentioned meta-phenylenediamines, meta-aminophenols, meta-diphenols and heterocyclic couplers such as for example indole derivatives, indoline derivatives, and their acid addition salts.

These couplers are preferably chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, and their acid addition salts.

When they are present, these additional couplers preferably represent approximately from 0.0005 to 5% by weight of the total weight of the dyeing composition, and still more preferably approximately from 0.005 to 3% by weight of this weight.

The acid addition salts of the oxidation base(s) and/or of the additional couplers which can be used in the dyeing composition of the invention are preferably chosen from hydrochlorides, hydrobromides, sulphates, tartrates, lactates and acetates.

The medium suitable for dyeing, or vehicle, preferably comprises water or a mixture of water and at least one organic solvent to solubilize compounds which might not be sufficiently soluble in water. As an organic solvent, there may be mentioned, for example, $C_1$–$C_4$ lower alkanols such as ethanol and isopropanol; glycerol; glycols and glycol ethers such as 2-butoxyethanol, propylene glycol, propylene glycol monomethyl ether and diethylene glycol monoethyl ether and monomethyl ether; as well as aromatic alcohols such as benzyl alcohol or phenoxyethanol, similar products and mixtures thereof.

Solvents may be present in proportions preferably ranging approximately from 1 to 40% by weight relative to the total weight of the dyeing composition, and still more preferably ranging approximately from 5 to 30% by weight.

The pH of the dyeing composition according to the invention preferably ranges from 3 to 12. The pH may be adjusted to the desired value by means of acidifying or alkalinizing agents customarily used in the dyeing of keratinous fibers.

Among acidifying agents, there may be mentioned, by way of example, inorganic or organic acids such as hydrochloric acid, orthophosphoric acid, carboxylic acids such as tartaric acid, citric acid and lactic acid, and sulphonic acids.

Among alkalinizing agents, there may be mentioned, by way of example, aqueous ammonia, alkali metal carbonates, alkanolamines such as mono-, di- and triethanolamines, as well as their derivatives, sodium or potassium hydroxide and compounds of the formula (V):

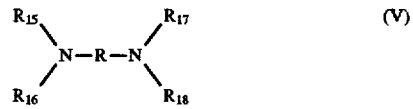

(V)

in which R is a propylene residue which may be substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

The dyeing composition according to the invention can also contain various adjuvants traditionally used in compositions for the dyeing of hair, such as anionic, cationic, nonionic, amphoteric or zwitterionic surfactants or mixtures thereof; anionic, cationic, nonionic, amphoteric or zwitterionic polymers or mixtures thereof; inorganic or organic thickening agents; antioxidants; penetrating agents; sequestering agents; perfumes; buffers; dispersing agents; conditioners such as silicones; film-forming agents; preservatives; and opacifying agents.

Of course, a person skilled in the art will be careful to choose the possible additional compound(s) mentioned above so that the advantageous properties intrinsically associated with the dyeing composition according to the invention are not, or are not substantially, altered by the addition (s) envisaged.

The dyeing composition according to the invention may be presented in various forms, for example in the form of a liquid, a cream, or a gel, or in any other form suitable for dyeing keratinous fibers, and human hair in particular.

Another subject of the present invention is the use of at least one N-substituted derivative of 4-hydroxyindole of formula (I) above or an acid addition salt thereof, as a coupler, in combination with at least one oxidation base, for the oxidation dyeing of keratinous fibers, and in particular human keratinous fibers, such as hair.

Another subject of the invention is a process for the oxidation dyeing of keratinous fibers, and in particular human keratinous fibers such as hair, which employs the dyeing composition as defined above.

According to this process, an effective amount to develop a color of at least one dyeing composition as defined above is applied to the fibers, the color is then developed at an acidic, neutral or alkaline pH using an effective amount of an oxidizing agent which is either added to the dyeing composition just at the time of use or which is present in an oxidizing composition that is applied to the fibers either separately from the dyeing composition at the same time that the dyeing composition is applied to the hair or sequentially with the dyeing composition.

According to a particularly preferred embodiment of the dyeing process according to the invention, the dyeing composition described above is mixed at the time of use with an oxidizing composition containing, in a medium suitable for dyeing, at least one oxidizing agent present in an amount sufficient to develop a coloration. The mixture obtained is then applied to the keratinous fibers and left in place for approximately from 3 to 50 minutes, preferably approximately from 5 to 30 minutes, after which the hair is rinsed, washed with shampoo, rinsed again and dried.

The oxidizing agent present in the oxidizing composition as defined above may be chosen from the oxidizing agents traditionally used for the oxidation dyeing of keratinous fibers, among which hydrogen peroxide, urea peroxide, alkali metal bromates and persalts such as perborates and persulphates, may be preferably mentioned. Of these, hydrogen peroxide is particularly preferred.

The pH of the oxidizing composition containing the oxidizing agent as defined above, is such that, after mixing with the dyeing composition, the pH of the resulting composition applied to the keratinous fibers preferably ranges approximately from 3 to 12, and still more preferably ranges from 5 to 11. The pH is adjusted to the desired value by means of acidifying or alkalinizing agents customarily used in the dyeing of keratinous fibers, and such as are defined above.

The oxidizing composition as defined above can also contain various adjuvants traditionally used in compositions for the dyeing of hair, and such as are defined above.

The composition which is finally applied to the keratinous fibers may be presented in various forms, for example in the form of a liquid, a cream, a gel, or in any other form suitable for carrying out a dyeing of keratinous fibers, and human hair in particular.

Another subject of the invention is a multi-compartment device or dyeing "kit" or any other multi-compartment packaging system containing at least two compartments, a first compartment of which contains the dyeing composition as defined above and a second compartment of which contains the oxidizing composition as defined above. These devices may be equipped with a means enabling the desired mixture to be delivered onto the hair, such as the devices described in French Patent No. FR-2,586,913 in the name of the Inventors, the disclosure of which is incorporated herein by reference.

Some compounds of the formula (I), which are used as couplers within the framework of the present invention, are new and, in this capacity, constitute another subject of the invention.

These new N-substituted derivatives of 4-hydroxyindole and their acid addition salts have the formula (I'):

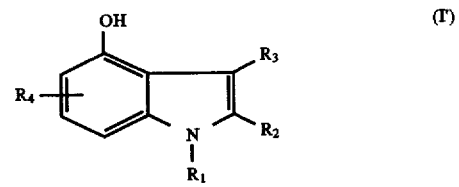

in which:

$R_1$ represents a $C_1$–$C_4$ monohydroxyalkyl radical; a $C_2$–$C_4$ polyhydroxyalkyl radical; a $C_1$–$C_4$ alkoxy($C_1$–$C_4$)-alkyl radical; a $C_1$–$C_4$ hydroxyalkoxy($C_1$–$C_4$)alkyl radical; a $C_1$–$C_4$ aminoalkyl radical; a $C_1$–$C_4$ aminoalkyl radical whose amine is mono- or disubstituted with a $C_1$–$C_4$ alkyl group, with an acetyl group, with a $C_1$–$C_4$ monohydroxyalkyl group or with a $C_2$–$C_4$ polyhydroxyalkyl group; a $C_1$–$C_4$ alkyl($C_1$–$C_4$)thioalkyl radical; a $C_1$–$C_4$ monohydroxyalkyl($C_1$–$C_4$)thioalkyl radical; a $C_2$–$C_4$ polyhydroxyalkyl($C_1$–$C_4$)thioalkyl radical; a $C_1$–$C_4$ carboxyalkyl radical; a $C_1$–$C_4$ alkoxy($C_1$–$C_4$)- carbonylalkyl radical; a $C_1$–$C_4$ acetylaminoalkyl radical; a $C_1$–$C_4$ cyanoalkyl radical; a $C_1$–$C_4$ trifluoroalkyl radical; a $C_1$–$C_4$ haloalkyl radical; a $C_1$–$C_4$ phosphoalkyl radical; or a $C_1$–$C_4$ sulphoalkyl radical;

$R_2$ and $R_3$, which are identical or different, represent a hydrogen or halogen atom; or a $C_1$–$C_4$ alkyl, a carboxyl, a $C_1$–$C_4$ alkoxycarbonyl or a formyl radical;

$R_4$ represents a hydrogen or halogen atom; a $C_1$–$C_4$ alkyl radical; a $C_1$–$C_4$ alkoxy radical; an acetylamino radical; a $C_1$–$C_5$ monohydroxyalkyl radical; a $C_2$–$C_4$ polyhydroxyalkyl radical; a $C_1$–$C_4$ alkoxy($C_1$–$C_4$)alkyl radical; a thiophene radical; a furan radical; a phenyl radical; a $C_7$–$C_{10}$ aralkyl radical; a phenyl or $C_7$–$C_{10}$ aralkyl radical which is substituted with a halogen atom, a $C_1$–$C_4$ alkyl radical, a trifluoromethyl radical, a $C_1$–$C_4$ alkoxy radical, an amino radical, or an amino radical mono- or disubstituted with a $C_1$–$C_4$ alkyl radical; a $C_1$–$C_4$ alkyl($C_1$–$C_4$)aminoalkyl radical; or a $C_1$–$C_4$ dialkyl($C_1$–$C_4$)aminoalkyl radical;

wherein when $R_2$ and $R_4$ simultaneously represent a hydrogen atom, and $R_1$ represents a methoxymethyl or (γ-chloro-β-hydroxypropyl) group, $R_3$ cannot represent a formyl radical; and wherein when $R_2$, $R_3$ and $R_4$ simultaneously represent a hydrogen atom, $R_1$ cannot represent a dimethylaminoethyl radical.

Among the new N-substituted derivatives of 4-hydroxyindole of formula (I'), there may preferably be mentioned:

4-hydroxy-1-N-(β-hydroxyethyl)indole,
4-hydroxy-1-N-(β-hydroxypropyl)indole,
1-N-(β,γ-dihydroxypropyl)-4-hydroxyindole,
4-hydroxy-1-N-(β-hydroxyethyl)-5-methylindole,
4-hydroxy-1-N-(β-hydroxypropyl)-5-methylindole,
1-N-(β,γ-dihydroxypropyl)-4-hydroxy-5-methylindole,
4-hydroxy-1-N-(β-hydroxyethyl)-6-methylindole,
4-hydroxy-1-N-(β-hydroxypropyl)-6-methylindole,
1-N-(β,γ-dihydroxypropyl)-4-hydroxy-6-methylindole,
5-benzyl-4-hydroxy-1-N-(β-hydroxyethyl)indole,
5-benzyl-4-hydroxy-1-N-(β-hydroxypropyl)indole,
5-benzyl-1-N-(β,γ-dihydroxypropyl)-4-hydroxyindole,
4-hydroxy-1-N-(β-hydroxyethyl)-5-β-hydroxyethylindole,
4-hydroxy-5-β-hydroxyethyl-1-N-(β-hydroxy-propyl)indole,
1-N-(β,γ-dihydroxypropyl)-4-hydroxy-5-β-hydroxyethylindole,
4-hydroxy-1-N-(β-hydroxyethyl)-5-β,γ-dihydroxypropylindole,
4-hydroxy-1-N-(β-hydroxypropyl)-5-β,γ-dihydroxypropylindole,
1-N-(β,γ-dihydroxypropyl)-4-hydroxy-5-β,γ-dihydroxypropylindole,
1-N-(γ-dimethylaminopropyl)-4-hydroxyindole,
1-N-ethylaminoethyl-4-hydroxyindole,
and the acid addition salts of these compounds.

Among these new N-substituted derivatives of 4-hydroxyindole of formula (I'), those which are more particularly preferred are:

4-hydroxy-1-N-(β-hydroxyethyl)indole,
4-hydroxy-1-N-(β-hydroxypropyl)indole,
1-N-(β,γ-dihydroxypropyl)-4-hydroxyindole,
4-hydroxy-1-N-(β-hydroxyethyl)-5-methylindole,
1-N-(γ-dimethylaminopropyl)-4-hydroxyindole,
and the acid addition salts of these compounds.

A further subject of the invention is a process for the preparation (main process) of the compounds of formula (I'), according to the synthesis scheme:

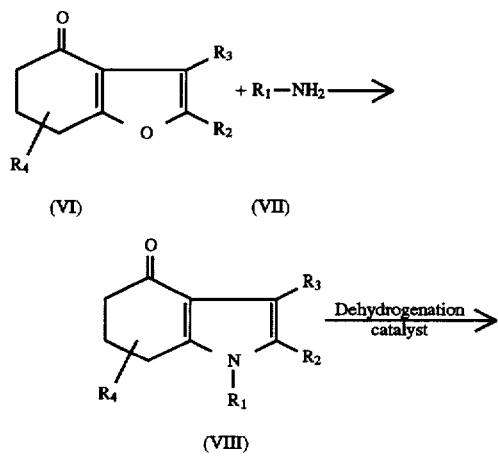

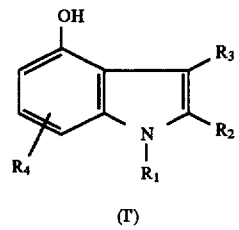

which comprises the steps of:

reacting, in a first stage, a 4-oxo-4,5,6,7-tetrahydrobenzofuran of formula (VI), in which the radicals $R_2$, $R_3$ and $R_4$ have the same meaning as in the formula (I') defined above, with a substituted amine of formula (VII) in which the $R_1$ radical has the same meaning as in the formula (I') defined above, in a solvent medium whose temperature preferably ranges from 80° to 160° C., to provide a 4-oxo-4,5,6,7-tetrahydroindole derivative of formula (VIII), in which the radicals $R_1$, $R_2$, $R_3$ and $R_4$ have the same meaning as in the formula (I') defined above; and in a second stage, aromatizing the compound of formula (VIII) by catalytic dehydrogenation in a solvent medium, at a temperature preferably ranging from 150° to 220° C., and more preferably ranging from 160° to 170° C., to provide a compound of formula (I') as defined above.

Among the solvents which may be used during the first stage, there may more particularly be mentioned lower alcohols such as ethanol, n-propanol, 1-butanol, 2-butanol, 2-methyl-1-butanol, 3-methyl-1-butanol, 2-methyl-1-propanol, n-pentanol, 2-pentanol, 3-methyl-3-pentanol, 4-methyl-2-pentanol, and 2-ethyl-1-butanol.

According to the process of the invention, any appropriate dehydrogenation catalyst may be used, for example a metal chosen from the group including manganese, platinum, palladium, rhodium, nickel, ruthenium, their oxides, and combinations of these metals and metal oxides.

The preferred dehydrogenation catalysts are palladium and platinum. In a known manner, the catalyst may be deposited on an inert support. Among these inert supports, there may be mentioned, for example, neutral wood charcoal, neutral charcoal, neutral alumina, zeolites, clays and the like. Neutral charcoal is preferably used.

The dehydrogenation catalysts are preferably present in a quantity ranging from 0.2 to 5% metal equivalent weight relative to the weight of the compound of formula (VIII) to be reacted.

The solvents used during the second stage are preferably chosen among solvents whose boiling point is greater than 150° C., such as for example diglyme whose boiling point (b.p.) is about 162° C. and diisobutyl ketone, whose b.p. is about 169° C.

According to a first variant of this main process, when in formula (VI) the radical $R_4$ is a hydrogen atom, it is possible to introduce a radical $R'_4$ in the 5-position, which radical is different from a hydrogen atom into the compounds of formula (VIII), by an aldolization reaction in a basic medium. This first variant corresponds to the synthesis scheme:

(VIII)    (IX)

(VIII')

(I")

which comprises the steps of:

reacting a compound of formula (VIII) and an aldehyde of formula (IX) in which the radical R'$_4$ represents a C$_1$–C$_3$ alkyl, C$_1$–C$_4$ monohydroxyalkyl, C$_2$–C$_3$ polyhydroxyalkyl, C$_1$–C$_3$ alkoxyalkyl, C$_1$–C$_4$ alkyl(C$_1$–C$_3$)-aminoalkyl, or C$_1$–C$_4$ dialkyl(C$_1$–C$_3$)aminoalkyl radical, in a basic medium, to obtain a compound of formula (VIII') in which the R'$_4$ radical has the same meaning as in formula (IX), and isomerizing the compound of formula (VIII') in an acidic medium according to conventional isomerization conditions, to provide a compound of formula (I") in which the radicals R$_1$, R$_2$ and R$_3$ have the same meanings as in formula (I'), and the radical R'$_4$ has the same meaning as in formula (IX).

The aldolization reaction is well known to a person skilled in the art and is described for example in European Patent Application No. EP-A-0,377,450, the disclosure of which is incorporated herein by reference.

According to a second variant of this main process, it is possible to functionalize the benzene portion of the compounds of formula (I') that are obtained from a compound of formula (VIII) in which R$_4$ represents a hydrogen atom to introduce a radical R$_4$ which is different from a hydrogen atom. This second variant corresponds to the synthesis scheme:

(VIII)    (I')

This second variant makes it possible, in particular, to introduce:

a dialkyl(C$_1$–C$_4$)aminomethyl-type substituent R$_4$ into the 5-position by a MANNICH reaction as described for example in the article by F. TROXLER & al., Helv. Chim. Acta, 51, (6), 1968, the disclosure of which is incorporated herein by reference;

an acetylamino-type substituent R$_4$ by a nitration reaction followed by a reducing reaction and an acetylation by conventional methods well known to a person skilled in the art; or a halogenated-type substituent R$_4$, obtained by a conventional halogenation reaction when the radicals R$_2$ and R$_3$ are both different from a hydrogen atom.

This list is of course not limiting in relation to the type of R$_4$ groups which can be directly introduced into the compounds of formula (I').

A further subject of the invention is intermediate compounds of formula (VIII), new per se, which have the formula (VIII"):

(VIII")

in which the radicals R$_1$, R$_2$, R$_3$ and R$_4$ have the same meanings as defined for the formula (I);

wherein when R$_2$ represents a methyl radical, R$_3$ represents a hydrogen atom or an ethyl radical, and R$_4$ represents a hydrogen atom, R$_1$ is other than a hydroxymethyl radical;

wherein when R$_2$ and R$_4$ simultaneously represent a hydrogen atom and R$_3$ represents a methyl radical, R$_1$ is other than a hydroxymethyl radical; and wherein when R$_2$, R$_3$ and R$_4$ simultaneously represent a hydrogen atom, R$_1$ is other than a β-chloroethyl radical.

These compounds of formula (VIII") can be used as intermediate compounds for the synthesis of the N-substituted derivatives of 4-hydroxyindole of formula (I).

The examples which follow are intended to illustrate the invention, no limitation of the scope being implied.

PREPARATION EXAMPLE 1

Synthesis of 4-hydroxy-1-N-(β-hydroxyethyl)indole a) Preparation of 4-oxo-4,5,6,7-tetrahydro-1-N-(β-hydroxyethyl)indole 80 g of ethanolamine were added to a solution of 136 g of 4-oxo-4,5,6,7-tetrahydrobenzofuran in 250 cm$^3$ of ethanol. The solution was heated at 130° C. for 6 hours. After allowing the reaction mixture to return to room temperature with stirring, the mixture was poured over a mixture of 800 cm$^3$ of isopropyl ether and 200 cm$^3$ of petroleum ether. A product crystallized with stirring, and then it was drained, washed with petroleum ether and dried under vacuum over phosphorus pentoxide. 160 g of the expected product was recovered, which product was recrystallized from 240 cm$^3$ of isopropanol. 150 g of the expected product was obtained whose melting point ranged from 96° to 97° C.

b) Preparation of 4-hydroxy-1-N-(β-hydroxyethyl) indole 15 g of palladium on carbon at 5% by weight and containing 50% of water were added to a solution of 25 g of 4-oxo-4,5,6,7-tetrahydro-1-N-(β-hydroxyethyl)indole, obtained in the preceding stage, in 300 cm³ of diglyme. The temperature of the mixture was raised and maintained at 162° C. for 10 hours. The mixture was then allowed to return to a temperature of 40° C. and then the catalyst was filtered off. The solvents were then removed under vacuum until 21.4 g of crude product were obtained which were taken up in a mixture of 30 cm³ of dichloromethane and 200 cm³ of petroleum ether. The crystals obtained were drained, washed with petroleum ether and then dried under vacuum over phosphorus pentoxide. 11 g of 4-hydroxy-1-N-(β-hydroxyethyl)indole were obtained whose elemental analysis, calculated for $C_{10}H_{11}NO_2$, was:

| % | C | H | N | O |
|---|---|---|---|---|
| Calculated | 67.78 | 6.26 | 7.90 | 18.06 |
| Found | 67.63 | 6.11 | 7.52 | 18.25 |

PREPARATION EXAMPLE 2

Synthesis of 4-hydroxy-1-N-(β-hydroxypropyl) indole

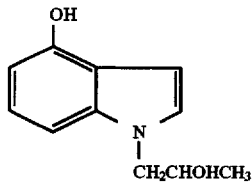

a) Preparation of 4-oxo-4,5,6,7-tetrahydro-1-N-(β-hydroxypropyl)indole 7.2 g of β-hydroxypropylamine were added to a solution of 13.6 g of 4-oxo-4,5,6,7-tetrahydrobenzofuran in 200 cm³ of ethanol. The solution was heated at 250° C. for 4 hours. The ethanol was then evaporated under vacuum. 18 g of an oil were obtained, which oil was used as it is in the next stage.

b) Preparation of 4-hydroxy-1-N-(β-hydroxypropyl) indole 10 g of palladium on carbon at 5% by weight and containing 50% water were added to a solution of 19.3 g of 4-oxo-4,5,6,7-tetrahydro-1-N-(β-hydroxypropyl)indole, obtained in the preceding stage, in 300 cm³ of diglyme. The temperature of the reaction medium was raised to the reflux temperature of diglyme for 5 hours, after removing the water by azeotropy. The catalyst was then filtered off on celite and then, the diglyme was evaporated off. 17 g of crude product were obtained. After chromatography on silica gel (heptane/ethyl acetate=¼), 15 g of viscous product were obtained, which product was crystallized by the addition of 15 cm³ of dichloromethane.

After filtration, washing with petroleum ether and drying under vacuum and over phosphorus pentoxide, 10 g of 4-hydroxy-1-N-(β-hydroxypropyl)indole were recovered whose melting point ranged from 93° to 95° C. and whose elemental analysis, calculated for $C_{11}H_{13}NO_2$, was:

| % | C | H | N | O |
|---|---|---|---|---|
| Calculated | 69.09 | 6.85 | 7.32 | 16.73 |
| Found | 69.08 | 7.00 | 7.25 | 16.73 |

PREPARATION EXAMPLE 3

Synthesis of 4-hydroxy-1-N-(β,γ-dihydroxypropyl) indole

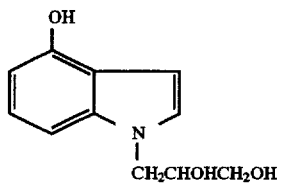

a) Preparation of 4-oxo-4,5,6,7-tetrahydro-1-N-(β,γ-dihydroxypropyl)indole 9.4 g of 2,3-dihydroxypropylamine were added to a solution of 13.6 g of 4-oxo-4,5,6,7-tetrahydrobenzofuran in 200 cm³ of ethanol. The reaction medium was heated at 150° C. for 9 hours. After evaporation of the solvent and purification of the crude product on silica gel (ethyl acetate/methanol=9/1), 11.2 g of 4-oxo-4,5,6,7-tetrahydro-1-N-(β,γ-dihydroxypropyl)indole were recovered in the form of an oil.

b) Preparation of 4-hydroxy-1-N-(β,γ-dihydroxypropyl)-indole 3.8 g of palladium on carbon at 5% by weight and containing 50% of water were introduced into a solution of 9.4 g of 4-oxo-4,5,6,7-tetrahydro-1-N-(β,γ-dihydroxypropyl)-indole, obtained in the preceding stage, in 50 cm³ of diglyme. The temperature of the reaction medium was raised to the reflux temperature of diglyme and the water was distilled off by azeotropy. After 23 hours of reaction, the catalyst was filtered off on celite and then the diglyme was evaporated off under vacuum. The crude product obtained was chromatographed on silica gel (ethyl acetate/heptane=9/1). 4.2 g of 4-hydroxy-1-N-(β,γ-dihydroxypropyl)indole were obtained in the form of a very viscous oil whose analysis by $^1H$ and $^{13}C$ nuclear magnetic resonance was in conformity with the expected product.

FORMULATION EXAMPLES

Formulation Examples 1 (invention) and 2 (comparative)

The following dyeing compositions were prepared (contents in grams):

| Compositions | 1 | 2(*) |
|---|---|---|
| 4-hydroxy-1-N-(β-hydroxyethyl)indole | 0.886 | |
| 4-hydroxy-1-N-ethylindole | | 0.805 |
| Para-aminophenol | 0.545 | 0.545 |
| Common dyeing vehicle | () | () |
| Demineralized water q.s. | 100 g | 100 g |

(*): example not forming part of the invention
(**): common dyeing vehicle

| | 
|---|---|
| Polyglycerolated oleyl alcohol containing 2 mol of glycerol | 4.0 g |
| Polyglycerolated oleyl alcohol containing 4 mol of glycerol, containing 78% of active substances (AS) | 5.69 g AS |
| Oleic acid | 3.0 g |
| Oleylamine containing 2 mol of ethylene oxide, sold under the trade name ETHOMEEN O12 by the company AKZO | 7.0 g |
| Diethylaminopropyl laurylaminosuccinamate, sodium salt containing 55% of AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AS | 0.455 g AS |
| Ammonium acetate | 0.8 g |
| Antioxidant, sequestering agent | q.s. |
| Perfume, preservative | q.s. |
| Aqueous ammonia containing 20% of $NH_3$ | 10.0 g |

At the time of use, each of the dyeing compositions 1 and 2 was mixed with an equal weight of hydrogen peroxide at 20 volumes (6% by weight).

Each mixture obtained was applied for 30 minutes to locks of natural grey hair which was 90% white. After rinsing, washing with a standard shampoo and drying, the locks were dyed in the shades appearing in Table I below:

| Example | 1 | 2(*) |
|---|---|---|
| Shade obtained | Strong copper-colored red | Light copper-colored red |

(*): example not forming part of the invention

The locks thus dyed were then subjected to a test of resistance to light (Xenotest).

To this end, the dyed locks of hair were fixed onto a support (cardboard or plastic). These supports were placed on sample carriers which were made to turn around a Xenon lamp for a period of 40 hours at a relative humidity level of 25±5% and at a temperature of 42.5±2.5° C.

The color of the locks was evaluated in the MUNSELL system, before and after the test of resistance to light, by means of a MINOLTA CM 2002 colorimeter.

According to the MUNSELL notation, a color is defined by the expression HV/C, in which the three parameters denote, respectively, the tint or hue (H), the intensity or value (V) and the purity or chroma (C); the oblique stroke in this expression is simply a convention and does not indicate a ratio.

The difference in the color of each lock before and after the test of resistance to light reflects the degradation of the coloration due to the action of light and was calculated by applying the NICKERSON formula: $\Delta E = 0.4 \ Co\Delta H + 6\Delta V + 3 \Delta C$, as described for example in "Couleur, Industrie et Technique"; pages 14–17; vol. No. 5; 1978.

In this formula, $\Delta E$ represents the difference in color between two locks, $\Delta H$, $\Delta V$ and $\Delta C$ represent the variation in absolute value of the parameters H, V and C, and Co represents the purity of the lock relative to which it is desired to evaluate the difference in color (purity of the lock before the test).

The results are given in Table II below:

| EXAMPLE | Color before the test | Color after the test | Degradation of the coloration | | | |
|---|---|---|---|---|---|---|
| | | | ΔH | ΔV | ΔC | ΔE |
| 1 | 5.3 R 3.9/4.5 | 5.9 R 4.0/4.4 | 0.6 | 0.1 | 0.1 | 2.0 |
| 2(*) | 7.5 R 4.3/4.5 | 9.3 R 4.6/3.6 | 1.8 | 0.3 | 0.9 | 7.7 |

(*): example not forming part of the invention

It was observed that the coloration obtained with the dyeing composition of Example 1, according to the invention (containing 4-hydroxy-1-N-(β-hydroxyethyl)indole), stood the action of light much better than the coloration obtained with the dyeing composition of Example 2, not forming part of the invention, because it contains 4-hydroxy-1-N-ethylindole, a compound which does not correspond to formula (I) defined above, but which corresponds to a prior art compound as described in EP-A-428 441.

What is claimed is:

1. A dyeing composition for keratinous fibers, which comprises: at least one coupler selected from N-substituted 4-hydroxyindole compounds of formula (I) and acid addition salts of said compounds of formula (I):

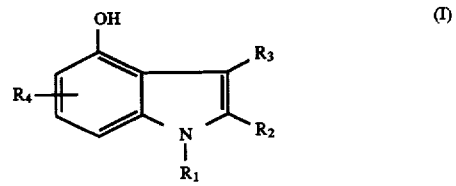

(I)

in which:

$R_1$ represents a $C_1$–$C_4$ monohydroxyalkyl radical; a $C_2$–$C_4$ polyhydroxyalkyl radical; a $C_1$–$C_4$ alkoxy($C_1$–$C_4$)alkyl radical; a $C_1$–$C_4$ hydroxyalkoxy($C_1$–$C_4$)alkyl radical; a $C_1$–$C_4$ aminoalkyl radical; a $C_1$–$C_4$ aminoalkyl radical whose amine is mono- or disubstituted with a substituent independently selected from a $C_1$–$C_4$ alkyl group, an acetyl group, a $C_1$–$C_4$ monohydroxyalkyl group and a $C_2$–$C_4$ polyhydroxyalkyl group; a $C_1$–$C_4$ alkyl($C_1$–$C_4$)thioalkyl radical; a $C_1$–$C_4$ monohydroxyalkyl($C_1$–$C_4$)thioalkyl radical; a $C_2$–$C_4$ polyhydroxyalkyl($C_1$–$C_4$)thioalkyl radical; a $C_1$–$C_4$ carboxyalkyl radical; a $C_1$–$C_4$ alkoxy($C_1$–$C_4$)carbonylalkyl radical; a $C_1$–$C_4$ acetylaminoalkyl radical; a $C_1$–$C_4$ cyanoalkyl radical; a $C_1$–$C_4$ trifluoroalkyl radical; a $C_1$–$C_4$ haloalkyl radical; a $C_1$–$C_4$ phosphoalkyl radical; or a $C_1$–$C_4$ sulphoalkyl radical;

$R_2$ and $R_3$, which are identical or different, represent a hydrogen or halogen atom; or a $C_1$–$C_4$ alkyl, a carboxyl, a $C_1$–$C_4$ alkoxycarbonyl or a formyl radical;

$R_4$ represents a hydrogen or halogen atom; a $C_1$–$C_4$ alkyl radical; a $C_1$–$C_4$ alkoxy radical; an acetylamino radical; a $C_1$–$C_5$ monohydroxyalkyl radical; a $C_2$–$C_4$ polyhydroxyalkyl radical; a $C_1$–$C_4$ alkoxy($C_1$–$C_4$)alkyl radical; a thiophene radical; a furan radical; a phenyl radical; a $C_7$–$C_{10}$ aralkyl radical; a phenyl or $C_7$–$C_{10}$ aralkyl radical which is substituted with at least one substituent selected from a halogen atom, a $C_1$–$C_4$ alkyl radical, a trifluoromethyl radical, a $C_1$–$C_4$ alkoxy radical, an amino radical and an amino radical mono- or independently disubstituted with a $C_1$–$C_4$ alkyl radical; a $C_1$–$C_4$ alkyl($C_1$–$C_4$)aminoalkyl radical; or a $C_1$–$C_4$ dialkyl($C_1$–$C_4$)aminoalkyl radical;

wherein for $R_1$–$R_4$ the alkyl and alkoxy groups are linear or branched and the halogen atoms are selected from chlorine, bromine, iodine and fluorine; and at least one oxidation base.

2. A dyeing composition according to claim 1, wherein said at least one coupler is selected from:

4-hydroxy-1-N-(β-hydroxyethyl)indole,
4-hydroxy-1-N-(β-hydroxypropyl)indole,
1-N-(β,γ-dihydroxypropyl)-4-hydroxyindole,
4-hydroxy-1-N-(β-hydroxyethyl)-5-methylindole,
4-hydroxy-1-N-(β-hydroxypropyl)-5-methylindole,
1-N-(β,γ-dihydroxypropyl)-4-hydroxy-5-methylindole,
4-hydroxy-1-N-(β-hydroxyethyl)-6-methylindole,
4-hydroxy-1-N-(β-hydroxypropyl)-6-methylindole,
1-N-(β,γ-dihydroxypropyl)-4-hydroxy-6-methylindole,
5-benzyl-4-hydroxy-1-N-(β-hydroxyethyl)indole,
5-benzyl-4-hydroxy-1-N-(β-hydroxypropyl)indole,
5-benzyl-1-N-(β,γ-dihydroxypropyl)-4-hydroxyindole,
4-hydroxy-1-N-(β-hydroxyethyl)-5-β-hydroxyethylindole,
4-hydroxy-5-β-hydroxyethyl-1-N-(β-hydroxy- propyl)indole,
1-N-(β,γ-dihydroxypropyl)-4-hydroxy-5-β-hydroxyethylindole,
4-hydroxy-1-N-(β-hydroxyethyl)-5-β,γ-dihydroxypropylindole,
4-hydroxy-1-N-(β-hydroxypropyl)-5-β,γ-dihydroxypropylindole,
1-N-(β,γ-dihydroxypropyl)-4-hydroxy-5-β,γ-dihydroxypropylindole,
1-N-(γ-dimethylaminopropyl)-4-hydroxyindole,
1-N-ethylaminoethyl-4-hydroxyindole, and the acid addition salts of said compounds.

3. A dyeing composition according to claim 2, wherein said at least one coupler is selected from:

4-hydroxy-1-N-(β-hydroxyethyl)indole,
4-hydroxy-1-N-(β-hydroxypropyl)indole,
1-N-(β,γ-dihydroxypropyl)-4-hydroxyindole,
4-hydroxy-1-N-(β-hydroxyethyl)-5-methylindole,
1-N-(γ-dimethylaminopropyl)-4-hydroxyindole, and the acid addition salts of said compounds.

4. A dyeing composition according to claim 1, wherein the acid addition salts of said compounds of formula (I) are selected from hydrochlorides, hydrobromides, sulphates and tartrates.

5. A dyeing composition according to claim 1, wherein said at least one coupler represents approximately from 0.0005 to 12% by weight of the total weight of the dyeing composition.

6. A dyeing composition according to claim 5, wherein said at least one coupler represents approximately from 0.005 to 6% by weight of the total weight of the dyeing composition.

7. A dyeing composition according to claim 1, wherein said at least one oxidation base is selected from para-phenylenediamines, bis-phenylalkylenediamines, para-aminophenols, ortho-aminophenols, heterocyclic bases, and the acid addition salts of said compounds.

8. A dyeing composition according to claim 1, wherein said at least one oxidation base represents approximately from 0.0005 to 12% by weight of the total weight of the dyeing composition.

9. A dyeing composition according to claim 8, wherein said at least one oxidation base represents approximately from 0.005 to 6% by weight of the total weight of the dyeing composition.

10. A dyeing composition according to claim 1, which further comprises at least one additional compound selected from coupler compounds which are different from the N-substituted 4-hydroxyindole compounds of formula (I) and the acid addition salts of said compounds of formula (I) and from direct dyes.

11. A dyeing composition according to claim 1, wherein said dyeing composition further comprises a medium suitable for dyeing.

12. A dyeing composition according to claim 1, which has a pH ranging from 3 to 12.

13. A dyeing composition according to claim 1, which is provided in the form of a liquid, a cream, a gel, or in any other form suitable for dyeing keratinous fibers.

14. A process for the oxidation dyeing of keratinous fibers, comprising the steps of:

applying to said keratinous fibers an effective amount to develop a color of at least one dyeing composition according to claim 1; and developing a color at acidic, neutral or alkaline pH using an effective amount of an oxidizing agent which is either added to said dyeing composition at the time of application or is present in an oxidizing composition that is applied to said keratinous fibers either separately from the dyeing composition but at the same time that said dyeing composition is applied to the fibers or sequentially with the dyeing composition.

15. A process according to claim 14, wherein said dyeing composition is mixed at the time of application with said oxidizing composition and said mixture is then applied to said fibers and allowed to remain in contact with said fibers for a time period ranging from 3 to 50 minutes to develop said color.

16. A process according to claim 15, wherein said mixture is allowed to remain in contact with said fibers for a time period ranging from 5 to 30 minutes to develop said color.

17. A process according to claim 15, wherein after said time period, said fibers are rinsed, washed with shampoo, rinsed again and dried.

18. A process according to claim 14, wherein said oxidizing agent is selected from hydrogen peroxide, urea peroxide, alkali metal bromates, and persalts.

19. A process according to claim 18, wherein said persalts are selected from perborates and persulphates.

20. A multi-compartment device or multi-compartment dyeing kit, comprising at least two compartments, wherein a first compartment contains a dyeing composition as defined in claim 1, and a second compartment contains an oxidizing composition.

21. A composition according to claim 11, wherein said medium suitable for dyeing comprises water or a mixture of water and at least one organic solvent selected from $C_1$–$C_4$ lower alkanols, glycerol, glycols, glycol ethers, and aromatic alcohols.

* * * * *